United States Patent
Diemunsch et al.

(10) Patent No.: US 8,708,949 B2
(45) Date of Patent: Apr. 29, 2014

(54) METHOD AND APPARATUS FOR INSUFFLATING A BODY CAVITY

(75) Inventors: Pierre Diemunsch, Strasbourg (FR); Pavel Novak, Stetten (CH)

(73) Assignee: Storz Endoskop Produktions GmbH (DE)

( * ) Notice: Subject to any disclaimer, the term of this patent is extended or adjusted under 35 U.S.C. 154(b) by 2447 days.

(21) Appl. No.: 11/038,325

(22) Filed: Jul. 21, 2005

(65) Prior Publication Data

US 2007/0000300 A1    Jan. 4, 2007

Related U.S. Application Data

(63) Continuation of application No. PCT/EP03/07809, filed on Jul. 18, 2003.

(30) Foreign Application Priority Data

Jul. 19, 2002    (DE) .................................. 102 33 861

(51) Int. Cl.
*A61M 37/00*    (2006.01)
*A61B 5/00*    (2006.01)
*G01N 21/00*    (2006.01)

(52) U.S. Cl.
USPC ............................... 604/26; 600/300; 73/1.02

(58) Field of Classification Search
USPC .................... 604/23, 26; 600/300; 73/1.02
See application file for complete search history.

(56) References Cited

U.S. PATENT DOCUMENTS

| | | | |
|---|---|---|---|
| 5,098,375 A | 3/1992 | Baier | 604/23 |
| 5,139,478 A * | 8/1992 | Koninckx et al. | 604/26 |
| 5,328,458 A | 7/1994 | Sekino et al. | 604/23 |
| 5,360,396 A | 11/1994 | Chan | 604/26 |
| 5,514,087 A | 5/1996 | Jones | 604/26 |
| 5,810,759 A | 9/1998 | Merz | 604/4 |
| 6,305,212 B1 | 10/2001 | Drzewiecki | 73/23.2 |
| 6,344,648 B1 * | 2/2002 | Boucher et al. | 250/343 |
| 6,645,197 B2 * | 11/2003 | Garrison et al. | 606/1 |
| 2002/0183687 A1 * | 12/2002 | Koninckx | 604/24 |

FOREIGN PATENT DOCUMENTS

| | | |
|---|---|---|
| DE | 36 35 004 A1 | 4/1987 |
| DE | 39 22 746 C1 | 8/1990 |
| DE | 42 40 758 C2 | 12/1999 |
| DE | 693 25 037 T2 | 1/2000 |
| WO | WO 97/20591 | 6/1997 |
| WO | WO 00/74757 | 12/2000 |

OTHER PUBLICATIONS

K. Semm, Die Laparoskopie in der Gynakologie, Nov. 1967, Geburtshilfe und Frauenheilkunde, vol. 11, pp. 1029-1042.

\* cited by examiner

*Primary Examiner* — Kami A Bosworth
*Assistant Examiner* — Imani Hayman
(74) *Attorney, Agent, or Firm* — St. Onge Steward Johnston & Reens LLC

(57) ABSTRACT

An apparatus for insufflating a body cavity with an insufflation gas comprising an insufflation device for delivering the insufflation gas to the body cavity. To detect possibly critical states in the body cavity, the apparatus is designed to withdraw a measuring gas from the body cavity. A measuring device having a gas sensor serves for measuring an additional substance contained in the measuring gas in addition to the insufflation gas and for outputting a measuring signal as a function of the additional substance.

20 Claims, 3 Drawing Sheets

METHOD AND APPARATUS FOR INSUFFLATING A BODY CAVITY

CROSS-REFERENCE OF PENDING APPLICATION

This application is a continuation of pending international application PCT/EP2003/007809 filed on Jul. 18, 2003 which designates US and which claims priority of German patent application No. 102 33 861.2 filed on Jul. 19, 2002.

BACKGROUND OF THE INVENTION

The invention relates to an apparatus for insufflating a body cavity with an insufflation gas, comprising an insufflation device having a delivery line for delivering the insufflation gas to the body cavity. The invention further relates to a method for insufflating a body cavity with an insufflation gas, said method comprising the following step: provision, by an insufflation device, of an insufflation gas for delivery to a body cavity.

Such an insufflation apparatus and such a method are known, for example, from the article entitled "Die Laparoskopie in der Gynätkologie" by K. Semm in "Geburtshilfe und Frauenheilkunde", volume 11, November 1967. With the aid of the insufflation device, the so-called insufflator, an insufflation gas, usually carbon dioxide gas ($CO_2$ gas), is introduced into a body cavity of a human or animal, for example into the abdominal cavity. The insufflation gas inflates the abdominal cavity so as to create the viewing and operating space which is needed between the internal organs and the abdominal wall in order to permit examination or surgery with the aid of an endoscope.

In addition to the insufflation gas, it is also possible that other gases will collect in the abdomen, for example nitrous oxide ($N_2O$) and/or methane ($MH_4$), which can result in explosive gas mixtures within the abdomen. Gas explosions may therefore occur, especially in connection with electro-surgical procedures.

Nitrous oxide is used for anaesthesia. It can diffuse from the bloodstream into the intra-abdominal cavity. If a nitrous oxide concentration of ca. 29% is exceeded, there is an increased risk of explosion of the gas mixture located in the abdominal area. The diffusion behavior of nitrous oxide in the abdominal area of pigs is known from the article "Nitrous Oxide Fraction in the Carbon Dioxide Pneumoperitoneum During Laparoscopy Under General Inhalation Anaesthesia in Pigs" by P. Diemunsch, Klaus D. Torp, T. Van Dorsselaer, D. Mutter, A. M. Diemunsch, R. Schaeffer, G. Teller and A. Van Dorsselaer. The article describes how, with the aid of a catheter and a gastight syringe, samples were taken from the abdominal cavities of pigs at ten-minute intervals. Nitrous oxide was used for anaesthesia. The abdominal cavities were inflated with carbon dioxide gas. The behavior of the nitrous oxide concentration in the abdomen was observed over a particularly long observation period. After approximately two hours, the critical limit of 29% nitrous oxide concentration is reached. After about nine hours, the nitrous oxide concentration rises to a value of just over ca. 66%.

The measuring method described in the article involving a catheter and a gastight syringe may well be acceptable for a scientific test. However, such an approach is not suitable for a typical endoscopic procedure in which the patient must be treated with great care and in which the operating physician must focus his concentration entirely on the patient.

A further problem in intra-abdominal interventions is that the patient's intestine may inadvertently be damaged or perforated. This danger is particularly great when using electrosurgery instruments. Damage to the intestine results in the escape of intestinal gases which contain methane. The methane can cause explosions. However, a far greater problem is that of the damage to the intestine not being detected during the intervention. In the postoperative period, this can lead to serious complications, or even to the death of the patient. However, an analysis of the gases in the abdominal area in the manner known from the abovementioned article is on account of the complicated collection of samples not really practicable with respect to methane.

It is therefore an object of the invention to permit early and reliable detection of any complications which may occur during an intervention in which an insufflation gas is insufflated into a body cavity, in particular into the abdominal cavity, of a human or animal.

SUMMARY OF THE INVENTION

According to the invention, the object is achieved by the fact that, in the apparatus mentioned at the outset, the insufflation device has a withdrawal line for withdrawing a measuring gas from the body cavity, and by a measuring device for measuring an additional substance contained in the measuring gas in addition to the insufflation gas and for outputting a measuring signal as a function of the additional substance, wherein the measuring device comprises a gas sensor.

Correspondingly, in the method mentioned at the outset, the object is achieved by the following further steps: providing a measuring gas, withdrawn from the body cavity, by the insufflation device, for a measuring device; measuring an additional substance contained in addition to the insufflation gas in the measuring gas and outputting a measuring signal as a function of the additional substance.

An underlying concept of the invention is the combined realization of the insufflation of the body cavity with an insufflation gas and the analysis of the gas mixture located there. The insufflation device and the measuring device are used jointly. During the intervention in the body cavity, in particular in an abdominal cavity, the physician carrying out the procedure is kept aware of the gas conditions present in said cavity at all times, as a result of which critical situations during and after the intervention can be avoided.

For example, it is possible to determine whether an explosive gas mixture has collected in the abdomen. Accordingly, the delivery of the insufflation gas can for example be increased and the body cavity at the same time ventilated, as a result of which the concentration of combustible gases in the abdomen decreases. A possible explosion can be reliably avoided in this way.

Any damage to the patient's intestine can be detected during the intervention. Countermeasures can be taken immediately, as a result of which postoperative complications, possibly even including the death of the patient, can be avoided.

A further important aspect of the invention is ventilation of the body cavity by withdrawal of the measuring gas. This way, the formation of explosive gas mixtures in the body cavity is prevented.

In a modular concept, measuring devices of different configurations can readily be used. For example, depending on requirements, a measuring device for the detection of nitrous oxide and/or a measuring device for the determination of intestinal gases, for example methane, can be used on the insufflation device according to the invention. In addition, the insufflation device can also be used on a stand-alone basis that is to say without a measuring device coupled to it, if in individual cases it is not necessary to analyze the gas mixture located in the abdominal area. The insufflation device can then even operate in a purely ventilating mode in which the withdrawn measuring gas, which in principle here forms a ventilation gas, is withdrawn from the body cavity only for ventilation purposes and is not analyzed for additional substances.

In one embodiment of the invention, the insufflation device comprises an insufflation cannula which at least partially houses both the delivery line and the withdrawal line.

This measure has the advantage, in handling terms, that only a single insufflation cannula is to be introduced into the body cavity. The patient is accessed at just one site by the introduction of the insufflation cannula. In principle, however, it would also be possible to use separate cannulas in each case for delivering the insufflation gas to the body cavity and for withdrawing the measuring gas from the body cavity.

In a further embodiment of the invention, the insufflation device comprises a tubing which at least partially houses both the delivery line and the withdrawal line.

This measure too is advantageous with respect to handling. A number of cannulas, for example a delivery cannula for delivering the insufflation gas to the body cavity and a withdrawal cannula for withdrawing the measuring gas from the body cavity, can be attached to the tubing which is, for example, a tubing with multiple lumens. However, it is particularly advantageous to use a "combined" insufflation cannula according to the aforementioned embodiment of the invention in which a delivery line as well as a withdrawal line is provided.

In a further embodiment of the invention, the measuring device comprises an alarm device for outputting an alarm signal when a predetermined limit value of the additional substance detected by the measuring device is exceeded.

Correspondingly, the step of outputting a measuring signal comprises outputting an alarm signal when a predetermined limit value of the additional substance detected by the measuring device is exceeded.

By means of this measure, the operating physician directly obtains an alarm signal if a critical situation arises in the body cavity being treated, for example if an explosive gas mixture has formed or if the patient's intestine has been damaged.

The following embodiments of the invention concern advantageous configurations of the gas sensor.

In an embodiment of the invention, the gas sensor is a gas chromatograph.

The gas chromatograph is, for example, a capillary gas chromatograph. A gas chromatograph permits a particularly accurate analysis of the measuring gas.

In a further embodiment of the invention, the gas sensor is a mass spectrometer.

This embodiment of the invention also permits an exact analysis of the measuring gas.

In a further embodiment of the invention, the gas sensor is designed to detect whether the measuring gas is combustible.

With this measure, explosive gas mixtures in the treated body cavity can be effectively avoided. In this connection, it is possible that the gas sensor does not determine in detail the nature and concentration of combustible gases in the measuring gas, but instead only determines whether the measuring gas as a whole is combustible.

In a further embodiment of the invention, the gas sensor is designed to detect a compound selected from the group consisting of methane ($CH_4$), nitrous oxide ($N_2O$) and mixtures thereof.

As has already been explained, the detection of methane in the measuring gas permits early detection of possible damage to the intestine. These gases are primarily responsible for the fact that burns or even explosions can occur in the body cavity.

It will be appreciated that the gas sensor can also be designed to determine further additional substances, for example different types of intestinal gases, oxygen ($O_2$), the insufflation gas, for example carbon dioxide gas ($CO_2$), hydrogen or the like. It is also possible to detect medicaments which have been administered to the patient and which are contained in the measuring gas.

In a further embodiment of the invention, the insufflation device comprises a pressure measuring device for measuring at least one of a pressure of the insufflation gas delivered to the insufflation cannula and of the measuring gas.

The pressure measuring device can, for example, be included in the insufflation device. However, it preferably forms a component part of the measuring device. In principle, however, it would also be possible to provide a pressure measuring device in the insufflation device as well as in the measuring device. A pressure measuring device is advantageous particularly with respect to the insufflation device. On the basis of the measuring results determined by the pressure measuring device, the insufflation device can monitor the pressure conditions in the body cavity and, if appropriate, deliver more or less insufflation gas to the body cavity.

In a further embodiment of the invention, the measuring device comprises a quantity measuring device for measuring a quantity of the measuring gas.

Just like a pressure measuring device according to the aforementioned embodiment of the invention, a quantity measuring device is able to control and monitor the pressure and quantity conditions of the insufflation gas in the body cavity.

In a further embodiment of the invention, the insufflation device is designed to control at least one of a quantity and the pressure of the insufflation gas to be delivered to the body cavity.

This measure is particularly advantageous in connection with the two aforementioned measures. The insufflation device evaluates the measuring results from the quantity measuring device and/or from the pressure measuring device and accordingly controls the delivery of the insufflation gas in the direction of the body cavity.

In a further embodiment of the invention, the insufflation device is designed to control a delivery of the insufflation gas to the body cavity as a function of the measuring signal generated by the measuring device relating to the additional substance.

Correspondingly, the method according to the invention is distinguished by the delivery of the insufflation gas to the body cavity being controlled as a function of the measuring signal relating to the additional substance.

Thus, for example, the delivery of the insufflation gas can be advantageously increased in order to lower the proportion of combustible gases in the body cavity in relation to the insufflation gas.

In this connection, it should also be noted that the insufflation device can in principle also be designed to control the withdrawal of the insufflation gas from the body cavity as a function of the measuring signal generated by the measuring device. With this measure too, it is possible to avoid potentially undesirable gas mixture situations in the body cavity.

In a further embodiment of the invention, the insufflation device is designed to deliver a substantially continuous stream of the insufflation gas to the body cavity.

Correspondingly, the step of providing an insufflation gas comprises generating a substantially continuous stream of the insufflation gas for insufflating the body cavity.

It would be possible, in principle, also to deliver the insufflation gas to the body cavity discontinuously, for example in the form of one or more pump impulses. However, such pump impulses are often associated with noise, which disturbs the operating physician during the endoscopic intervention. By contrast, a continuous delivery of the stream of insufflation gas to the body cavity is quiet, if not completely silent. In addition, vibrations, which possibly also impact the patient, are reduced or completely avoided.

In a further embodiment of the invention, the insufflation device is designed to withdraw a substantially continuous stream of the measuring gas.

Correspondingly, the step of providing a measuring gas comprises withdrawing a substantially continuous stream of the measuring gas.

Here, the same principle applies as in the aforementioned measure, namely that a continuous stream of gas is comparatively quiet and reduces any mechanical loads on patient and insufflation device.

"Continuous" in the context of the two aforementioned measures signifies that the respective stream of gas is not interrupted or is only rarely interrupted. Nevertheless, the gas volume delivered, that is to say the gas stream, can still be increased or decreased.

In a further embodiment of the invention, the apparatus provides an amount of measuring gas capable of ventilating the body cavity.

A deliberate gas leakage is thus provided in order to ventilate the body cavity. This ventilation prevents the formation of a potentially explosive gas mixture in the body cavity. It will be appreciated that the deliberate ventilation of the body cavity is to be advantageously combined with a correspondingly high delivery of insufflation gas to the body cavity. The withdrawn measuring gas is thus replaced by freshly delivered insufflation gas in the body cavity. It has been found that the withdrawal of approximately half a liter to one liter of measuring gas per minute is expedient. In this connection, it should also be mentioned that the measuring gas can in fact be pure insufflation gas if, for example, no nitrous oxide, intestinal gas or other substance diffuses into the insufflation gas insufflated into the body cavity.

A minimum gas flow for ventilating the body cavity, in particular a continuous stream of measuring gas, according to the advantageous embodiment of the invention makes it possible to deliver a comparatively large stream of insufflation gas to the body cavity. The insufflation gas can be at a comparatively high pressure. It is therefore possible to use thinner insufflation tubings and thinner insufflation cannulas, which are easier to handle and impose less stress on the patient. An insufflation cannula according to the invention and an insufflation tubing according to the invention, each provided with a delivery line for the insufflation gas and a withdrawal line for the measuring gas, are therefore comparatively thin, although two or more lines are provided. A multilumen insufflation cannula of this kind and a multilumen insufflation tubing of this kind are not thicker, or are at any rate not much thicker, than a conventional insufflation cannula and conventional insufflation tubing in which in each case only one line is provided. An insufflator with a multilumen insulation cannula and/or a multilumen insufflation tubing, which are designed for delivering an insufflation gas to a body cavity and at the same time for withdrawing an evacuation gas from the body cavity, in principle already constitute an invention in themselves.

In a further embodiment of the invention, the measuring device comprises a withdrawal pump for withdrawing the measuring gas.

Such a withdrawal pump can be provided both in the insufflation device and also in the measuring device. The withdrawal pump, which for example can be a small suction pump, ensures a minimum flow of measuring gas from the body cavity. The delivery volume of the pump can be adjustable.

It will be appreciated that the features mentioned above and the features still to be explained below can be used not only in the stated combinations, but also in other combinations or in isolation, without departing from the scope of the present invention.

BRIEF DESCRIPTION OF THE DRAWINGS

The invention is now described and explained in greater detail below on the basis of selected illustrative embodiments and with reference to the attached drawings, in which.

DETAILED DESCRIPTION OF PREFERRED EMBODIMENTS

Figure 1:
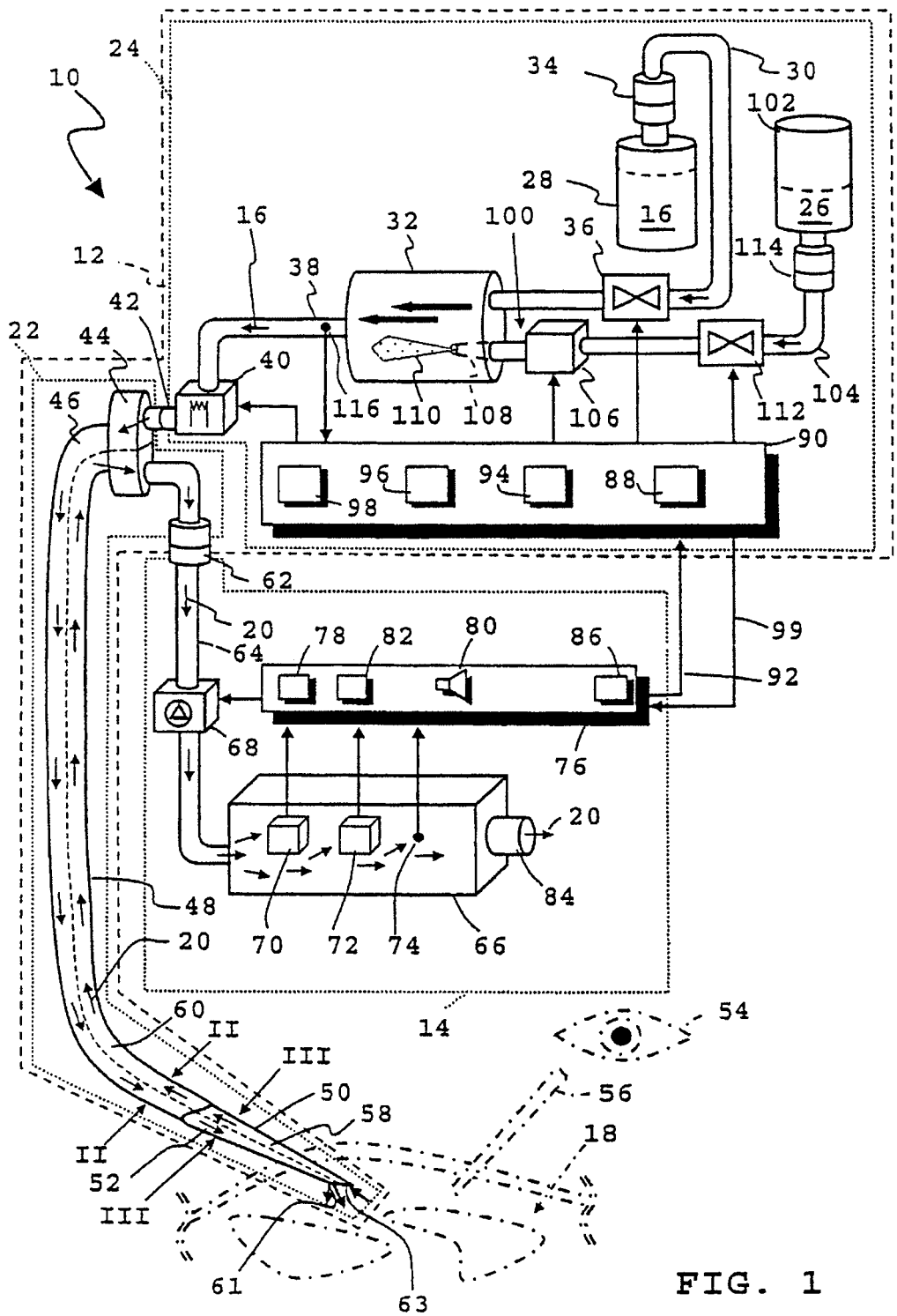
FIG. 1 shows a perspective view, very diagrammatically in part, of a first illustrative embodiment of an apparatus according to the invention for insufflating a body cavity with an insufflation gas.
Figure 2:
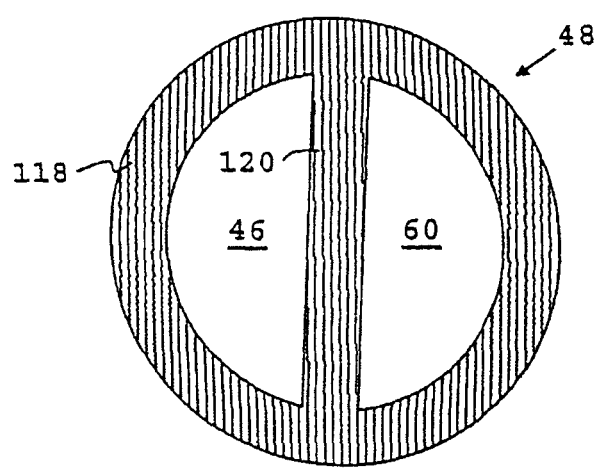
FIG. 2 shows a cross section, along a line II-II, of an insufflation tubing of the apparatus according to FIG. 1.
Figure 3:
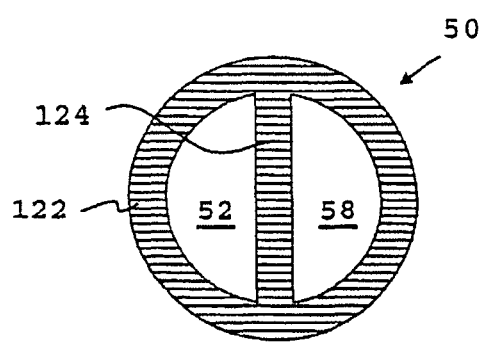
FIG. 3 shows a cross section, along a line III-III, of an insufflation cannula of the apparatus according to FIG. 1.

In FIGS. 1 through 3, an apparatus for insufflating a body cavity with an insufflation gas is indicated in its entirety by reference number 10.

The apparatus 10 follows a modular concept in which a measuring device 14 can be connected to an insufflation device 12. In the drawing, the measuring device 14 is shown in the state when connected to the insufflation device 12.

The insufflation device 12 is used for delivering an insufflation gas 16 to a body cavity 18, for example to the abdominal area, of a human or animal. In addition, the insufflation device 12 withdraws a measuring gas 20 from the body cavity 18 and transports this measuring gas 20 to the measuring device 14. To transports both gases 16, 20, the insufflation device 12 is provided with a combined delivery and withdrawal device 22 which, for the sake of simplicity, is referred to below as "delivery device 22". The delivery device 22 is attached to a preparation device 24, with which it can be connected in a releasable manner. The preparation device 24 is used for delivering the insufflation gas 16 to the delivery device 22. With the preparation device 24, it is possible to control the quantity and pressure of the insufflation gas 16 delivered to the delivery device 22. In addition, the preparation device 24 prepares the insufflation gas 16. In the illustrative embodiment, the preparation device 24 charges the insufflation gas 16 with a humidifying liquid 26.

The measuring device 14 is used to analyze the measuring gas 20. The measuring device 14 analyzes the measuring gas 20 and detects one or more additional substances contained in the measuring gas 20, for example nitrous oxide, methane or the like.

The functioning of the apparatus 10 is explained in greater detail below:

The insufflation gas 16, which can for example be carbon dioxide gas ($CO_2$), flows from a mainly cartridge-like storage vessel 28 through a line 30 to a preparation chamber 32 of the insufflation device 12. The storage vessel 28 is connected to the line 30 via a releasable connection, for example a screw-type or bayonet-type connection 34. Arranged on the line 30 there is a valve arrangement 36 with which the stream of insulation gas flowing into the preparation chamber 32 can be adjusted.

The insufflation gas 16 flows from the preparation chamber 32 and through a line 38 to a heater 40. The heater 40 is used to heat the insufflation gas 16 so that the latter is optimally adapted to the microclimate conditions in the body cavity 18. The heater 40 is releasably connected via an attachment piece 42 to an attachment device 44 of the delivery device 22. The attachment piece 42 and the attachment device 44 form, for example, a screw connection and/or plug connection.

From the attachment device 44, the insulation gas 16 flows through a delivery line 46 of a tubing 48 to an insulation cannula 50. The insufflation gas 16 flows through the insufflation cannula 50 via a delivery line 52 and emerges from the insulation cannula 50, at its front end remote from the tubing 48, into the body cavity 18. There, the insulation gas 16 forms an inflated space, so that an operating physician 54 can perform examinations, operations or the like with the aid of an endoscope 56.

In such an intervention, nitrous oxide ($N_2O$), for example, is used to anaesthetize the patient. It is further conceivable for the patient's intestine to be damaged during the intervention, as a result of which intestinal gases, in particular methane, pass into the body cavity 18. These additional substances (not detailed in the figure) can mix with the insufflated insufflation gas 16. Moreover, the insufflation gas 16 located in the body cavity 18 can be charged with particulate and/or liquid additional substances, for example with humidity present in the body cavity 18. Some of the gas located in the body cavity 18 is withdrawn from said body cavity 18 to the measuring device 14 with the aid of the delivery device 22, insofar as the latter constitutes a withdrawal device or includes a withdrawal device. The withdrawn gas constitutes the measuring gas 20.

The measuring gas 20 flows through a withdrawal line 58 of the insufflation cannula 50 to a withdrawal line 60 of the tubing 48, which is, for example, a multilumen tubing. The withdrawal line 60 opens into the attachment device 44 to which the measuring device 14 is connected via an attachment piece 62 of the measuring device 14. The attachment piece 62 and the attachment device 44 are, for example, screwed onto one another and/or plugged into one another.

Arranged on the attachment device 44 there is an outlet 61 which communicates with an inlet 63 of the attachment piece 62. The measuring gas 20 flows through the outlet 61 and the inlet 63. The measuring gas 20 flows from the attachment device 44 via the attachment piece 62 and via a line 64 to a measuring chamber 66 of the measuring device 14. Arranged on the line 64 there is a withdrawal pump 68 which sucks in the measuring gas 20 and pumps it into the measuring chamber 66. The withdrawal pump 68 conveys a continuous stream of measuring gas from the body cavity 18 to the measuring chamber 66.

It will be appreciated that the withdrawal pump 68 can in principle also operate in a discontinuous operating mode, for example in a pulsed mode or the like.

The measuring device 14 has an additive measuring device 70, a quantity measuring device 72 and a pressure measuring device 74. The devices 70, 72, 74 are arranged on the measuring chamber 66, the important point being that they come into contact there with the measuring gas 20.

The additive measuring device 70 includes, for example, a gas sensor, a gas chromatograph and/or a mass spectrometer. It will be appreciated that it is also possible for just one of the aforementioned instruments to be present in the additive measuring device 70. In a simple embodiment, for example, a gas sensor is provided which determines whether the measuring gas 20 is combustible and/or has an explosive consistency. Additional substances can also be present in the measuring gas 20 in addition to the insufflation gas 16, for example nitrous oxide, methane or the like, which can be determined by the additive measuring device 70.

The quantity measuring device 72 and the pressure measuring device 74 measure the quantity and the pressure, respectively, of the measuring gas 20. On the basis of the measuring values thus determined, the quantity and pressure ratios in the body cavity 18 can be determined. However, the determined measuring values can also be used to control and monitor the delivery of the insufflation gas 16 to the body cavity 18. An evaluation device 76 of the measuring device 14 serves to evaluate the measuring values determined by the measuring devices 70, 72, 74.

The evaluation device 76 has, for example, a display 78 and a speaker 80 as output devices with which can output the values determined by the devices 70, 72, 74. The speaker 80 is used, for example, to output an alarm sound or other alarm signal if a value determined by the additive measuring device 70 exceeds a predetermined limit value, for example if the measuring gas 20 is explosive. To input such limit values or for other operations, input devices 82 of the evaluation device 76 are used, which input devices 82 include, for example, function keys or the like. The measuring gas 20 can flow out of the measuring chamber 66 through an outlet 84.

A valve arrangement (not shown) for closing the outlet 84 can be arranged at this outlet 84. In any event, the body cavity 18 can be ventilated with the aid of the delivery and withdrawal device 22 and the measuring device 14.

The evaluation device 76 has a transmitter device 86 with which it can transmit messages to a receiver device 88 of a control device 90 of the insufflation device 12. The devices 86, 88 are connected to one another, for example, via one or more electrical lines and a releasable plug connection (not shown). The signals can in principle be each of the measuring signals generated by measuring devices 70, 72, 74. For example, a measuring signal 92 generated by the additive measuring device 70 is transmitted to the control device 90. The measuring signal 92 is dependent on one or more additional substances which are contained in addition to the insufflation gas 16 in the measuring gas 20, for example on the contentn of nitrous oxide in the measuring gas 20.

The control device 90 serves to control and monitor the insufflation device 12. It has input devices 94, for example function keys, and output devices 96, for example a display, LED or the like. In the present case, the control device 90, like the evaluation device 76, is a microprocessor control. A microprocessor 98 is indicated diagrammatically for the control device 90 only.

The control device 90 controls the valve arrangement 36 in order to influence the insufflation gas 16 to be delivered to the body cavity 18.

In addition, the control device 90 controls and monitors a humidifying apparatus 100 used for humidifying the insufflation gas 16. Alongside the preparation chamber 32 there is a cartridge-like storage vessel 102 from which the humidifying liquid 26 passes via a line 104 to an injector apparatus 106 and to the humidifying apparatus 100. The injector apparatus 106 has an injector outlet 108 opening into the preparation chamber 32. The injector apparatus 106 sprays a humidifying mist 110 through the injector outlet 108, and this humidifying mist 110 is entrained by the insufflation gas 16 and conveyed to the body cavity 18. There, the humidifying liquid 16 ensures advantageous microclimate conditions which result in a reduction in postoperative complications. Arranged on the line 104 there is a valve arrangement 112 with which the flow of the humidifying liquid 16 in the line 104 can be adjusted. The storage vessel 102 is connected to the line 104 via a releasable connection 116, for example a screw-type and/or plug-type connection.

Arranged on the line 38 there is a sensor 116 which determines the quantity and the pressure of the insufflation gas 16 conveyed from the insufflation device 12 to the body cavity 18. On the basis of the measuring values transmitted from the sensor 116 to the control device 90, the latter can control the quantity of the insufflation gas 16 conveyed to the body cavity 18. In addition, the control device 90 evaluates the measuring signal 92 coming from the measuring device 14. If, for example, the concentration of one or more additional substances contained in the measuring gas 20 increases in an undesired manner, the control device 90 can increase the stream of the insufflation gas 16 to the body cavity 18.

In this connection, it is possible in principle for the control device 90 to govern the measuring device 14 in an advantageous manner. For example, the control device 90 can govern the withdrawal pump 68 as a function of the stream of insufflation gas being delivered to the body cavity 18, in which case it transmits corresponding control signals via a control line 99. If more insufflation gas 16 is pumped to the body cavity 18, the withdrawal pump 68 correspondingly increases its delivery rate, and vice versa.

From the cross section in FIG. 2, it will be seen that the tubing 48 comprises the two lines 46 and 60 separate from one another. The tubing 48 is made of flexible material, for example rubber or plastic. The lines 46, 60 are formed within an outer jacket 118 and are separated from one another by a dividing wall 120. The tubing 48 preferably has a substantially circular cross section. The lines 46 and 60 each have semicircular cross sections. It will be appreciated that other cross-sectional shapes are also possible. Moreover, in contrast to the illustrative embodiment, the lines 46 and 60 can also have cross sections of different sizes. It is also possible for the tubing to comprise more than two lines.

FIG. 3 shows a cross section through the insufflation cannula 50 which is, for example, a trocar. In the insufflation cannula 50 there also are two lines, namely the delivery line 52 and the withdrawal line 58. The insufflation cannula 50 is made of metal, for example. In the illustrative embodiment, it has a similar cross-sectional configuration to that of the tubing 48, i.e. the two lines 52, 58 are formed within an elongate and substantially circular-cylindrical housing 122 and are separated from one another by a dividing wall 124.

The two lines 52, 58 preferably emerge directly alongside each other at the end of the insufflation cannula 50 remote from the tubing 48. In principle, however, it would also be possible to provide an insufflation cannula in which, as in the illustrative embodiment, a number of lines are provided, but in which these lines emerge from the insufflation cannula at positions relatively far apart from one another, at any rate not immediately adjacent. For example, as in the illustrative embodiment, the outlet of an insufflation line could be arranged at the front end of an insufflation cannula, whereas an inlet or a number of inlets for a measuring gas line could be arranged laterally on the insufflation cannula.

Figure 4:
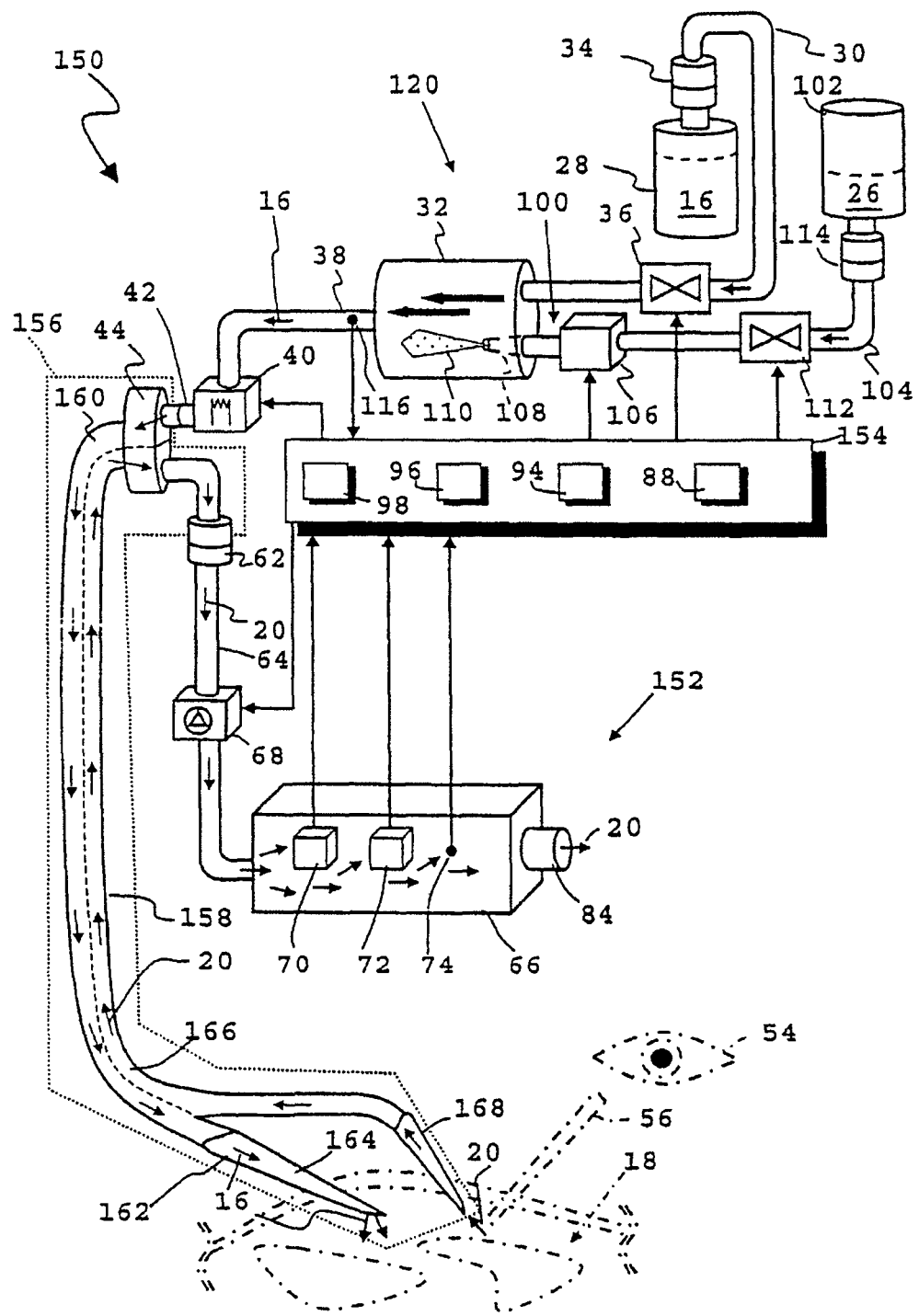
FIG. 4 shows a perspective view, very diagrammatically in part, of a second illustrative embodiment of an apparatus according to the invention for insufflating a body cavity with an insufflation gas.

In FIG. 4, a second illustrative embodiment of an apparatus according to the invention for insufflating a body cavity with an insufflation gas is indicated in its entirety by reference number 150.

The apparatus 150 mainly has similar components to those in the apparatus 10 according to FIGS. 1 through 3. Those components which have a similar function are indicated in FIG. 4 with the same reference numbers as in FIGS. 1 through 3 and, for the sake of simplicity, are not described in detail below.

In contrast to the apparatus 10, the apparatus 150 does not follow a modular design, and instead it forms an integrated solution in which a measuring device 152 is integrated permanently into the apparatus 150. The apparatus 150 has, for example, a housing (not shown in the figure) in which the measuring device 152 is contained. The measuring device 152 is otherwise basically similar to the measuring device 14, but in contrast to the latter it does not have its own evaluation device comparable to the evaluation device 76.

In the apparatus 150, the functions of an evaluation device are performed by a control device 154 which otherwise has basically the same functions as the control device 90.

Instead of the delivery device 22, the apparatus 150 has a delivery and withdrawal device 156 which, for simplicity, is referred to below as "delivery device 156".

The delivery device 156 comprises a tubing 158 in which a delivery line 160 is provided for delivering the insufflation gas 16 to an insufflation cannula 162. In contrast to the insufflation cannula 50, there is only one line in the insufflation cannula 162, namely a delivery line 164 which is connected to the delivery line 160 and which opens into the body cavity 18 at the end of the insufflation cannula 162 remote from the tubing 158.

In addition to the delivery line 160, the tubing 158 also has a withdrawal line 166 which is not however connected to the insufflation cannula 162 but instead to a withdrawal cannula 168. Through the withdrawal cannula 168 which, like the insulation cannula 162 in the position of use shown in FIG. 4, engages in the body cavity 18, it is possible to remove a gas from the body cavity 18, which is mainly the measuring gas 20. The withdrawal cannula 168 forms a withdrawal device. The measuring gas 20 flows from the withdrawal cannula 168 through the withdrawal line 166 to the measuring device 152 which analyzes the measuring gas 20 in the manner already discussed and ensures controlled evacuation of the body cavity 18.

In this connection, it should be noted that the measuring devices 14 and 154 can be operated in different operating modes. For example, they can be operated in a purely analytical mode, in which relatively small quantities of measuring gas 20 are sufficient for analysis and correspondingly small quantities of measuring gas 20 need to be withdrawn from the body cavity 18. However, a purely ventilating mode is also possible, in which the measuring gas 20 serves mainly to ventilate the body cavity 18. A relatively large quantity of measuring gas 20 is transported from the body cavity 18. The measuring gas 20 is not analyzed, or is analyzed only at random. However, a combined analysis and evacuation mode is preferred in which the measuring gas 20 serves on the one hand to evacuate the body cavity 18 and on the other hand is analyzed continuously or at short intervals.

What is claimed is:

1. An apparatus for insufflating a body cavity with an insufflation gas, comprising
   an insufflation device, having
   a delivery line for delivering the insufflation gas to the body cavity, and a withdrawal line for withdrawing a measuring gas from the body cavity; and a measuring device for measuring an additional substance contained in said measuring gas in addition to said insufflation gas and for outputting a measuring signal as a function of said additional substance, wherein said measuring device comprises a gas sensor designed to detect a compound selected from the group consisting of methane ($CH_4$), nitrous oxide ($N_2O$) and mixtures thereof.

2. The apparatus of claim 1, wherein said insufflation device comprises an insufflation cannula which at least partially houses both said delivery line and said withdrawal line.

3. The apparatus of claim 1, wherein said insufflation device comprises a tubing which at least partially houses both said delivery line and said withdrawal line.

4. The apparatus of claim 1, wherein said measuring device comprises an alarm device for outputting an alarm signal when a predetermined limit value of said additional substance detected by said measuring device is exceeded.

5. The apparatus of claim 1, wherein said gas sensor is a gas chromatograph.

6. The apparatus of claim 1, wherein said gas sensor is a mass spectrometer.

7. The apparatus of claim 1, wherein said gas sensor is designed to detect whether said measuring gas is combustible.

8. The apparatus of claim 1, wherein said insufflation device comprises a pressure measuring device for measuring a pressure of at least one of said insufflation gas to be delivered to said body cavity and of said measuring gas.

9. The apparatus of claim 1, wherein said measuring device comprises a quantity measuring device for measuring a quantity of said measuring gas.

10. The apparatus of claim 1, wherein said insufflation device is designed to control at least one of a quantity and a pressure of said insufflation gas to be delivered to said body cavity.

11. The apparatus of claim 1, wherein said insufflation device is designed to control a delivery of said insufflation gas to said body cavity as a function of said measuring signal generated by said measuring device relating to said additional substance.

12. The apparatus of claim 1, wherein said insufflation device is designed to deliver a substantially continuous stream of said insufflation gas to said body cavity.

13. The apparatus of claim 1, wherein said insufflation device is designed to withdraw a substantially continuous stream of said measuring gas.

14. The apparatus of claim 1, providing an amount of said measuring gas capable of ventilating said body cavity.

15. The apparatus of claim 1, wherein said measuring device comprises a withdrawal pump for withdrawing said measuring gas.

16. A method for measuring a state of an insufflation gas comprising the following steps:

providing the insufflation gas for delivery to a body cavity by an insufflation device, providing a measuring gas withdrawn from said body cavity for a measuring device by said insufflation device, measuring an additional substance contained in said measuring gas in addition to said insufflation gas, and outputting a measuring signal as a function of said additional substance, wherein said additional substance is selected from the group consisting of methane ($CH_4$), nitrous oxide ($N_2O$) and mixtures thereof.

17. The method of claim 16, wherein said step of outputting the measuring signal comprises outputting an alarm signal when a predetermined limit value of said additional substance detected by said measuring device is exceeded.

18. The method of claim 16, wherein a delivery of said insufflation gas to said body cavity is controlled as a function of said measuring signal relating to said additional substance.

19. The method of claim 16, wherein said step of providing the insufflation gas comprises generating a substantially continuous stream of said insufflation gas for insufflating said body cavity.

20. The method of claim 16, wherein said step of providing the measuring gas comprises withdrawing a substantially continuous stream of said measuring gas.

* * * * *